(12) United States Patent
Wall et al.

(10) Patent No.: US 8,437,450 B2
(45) Date of Patent: May 7, 2013

(54) FAST MEASUREMENT OF X-RAY DIFFRACTION FROM TILTED LAYERS

(75) Inventors: John Wall, Newton Aycliffe (GB); David Jacques, Durham (GB); Boris Yokhin, Nazareth Illit (IL); Alexander Krokhmal, Haifa (IL); Paul Ryan, Darlington (GB); Richard Bytheway, Durham (GB); David Berman, Tivon (IL); Matthew Wormington, Littleton, CO (US)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 340 days.

(21) Appl. No.: 12/958,420

(22) Filed: Dec. 2, 2010

(65) Prior Publication Data

US 2012/0140889 A1    Jun. 7, 2012

(51) Int. Cl.
*G01N 23/207*    (2006.01)

(52) U.S. Cl.
USPC ............................................ 378/73

(58) Field of Classification Search .......... 378/71, 378/73
See application file for complete search history.

(56) References Cited

U.S. PATENT DOCUMENTS

| | | |
|---|---|---|
| 2,805,342 A | 9/1957 | Lang |
| 4,242,588 A | 12/1980 | Silk et al. |
| 4,446,568 A | 5/1984 | Williams et al. |
| 4,696,024 A | 9/1987 | Pesch |
| 4,725,963 A | 2/1988 | Taylor et al. |
| 4,847,882 A | 7/1989 | Knoth et al. |
| 4,989,226 A | 1/1991 | Woodbury et al. |
| 5,151,588 A | 9/1992 | Kiri et al. |
| 5,340,988 A | 8/1994 | Kingsley et al. |
| 5,373,544 A | 12/1994 | Goebel |
| 5,481,109 A | 1/1996 | Ninomiya et al. |
| 5,530,732 A | 6/1996 | Takemi |
| 5,574,284 A | 11/1996 | Farr |
| 5,619,548 A | 4/1997 | Koppel |
| 5,740,226 A | 4/1998 | Komiya et al. |

(Continued)

FOREIGN PATENT DOCUMENTS

| | | |
|---|---|---|
| JP | 3075548 A | 3/1991 |
| JP | 5188019 A | 7/1993 |

(Continued)

OTHER PUBLICATIONS

Japanese Patent Application # 2006114489 Official Action dated Jun. 14, 2011.

(Continued)

*Primary Examiner* — Glen Kao
(74) *Attorney, Agent, or Firm* — D. Kligler I.P. Servies Ltd.

(57) ABSTRACT

A method for analysis includes directing a converging beam of X-rays toward a surface of a sample having multiple single-crystal layers, including at least a first layer and a second layer that is formed over and tilted relative to the first layer. The X-rays that are diffracted from each of the first and second layers are sensed simultaneously while resolving the sensed X-rays as a function of angle so as to generate a diffraction spectrum including at least a first diffraction peak due to the first layer and a second diffraction peak due to the second layer. The diffraction spectrum is analyzed so as to identify a characteristic of at least the second layer.

16 Claims, 5 Drawing Sheets

U.S. PATENT DOCUMENTS

| | | | |
|---|---|---|---|
| 5,850,425 | A | 12/1998 | Wilkins |
| 5,900,645 | A | 5/1999 | Yamada |
| 5,923,720 | A | 7/1999 | Barton et al. |
| 5,949,847 | A | 9/1999 | Terada et al. |
| 5,963,329 | A | 10/1999 | Conrad et al. |
| 6,041,098 | A | 3/2000 | Touryanski et al. |
| 6,192,103 | B1 | 2/2001 | Wormington et al. |
| 6,226,347 | B1 | 5/2001 | Golenhofen |
| 6,226,349 | B1 | 5/2001 | Schuster et al. |
| 6,317,483 | B1 | 11/2001 | Chen |
| 6,331,890 | B1 | 12/2001 | Marumo et al. |
| 6,381,303 | B1 | 4/2002 | Vu et al. |
| 6,389,102 | B2 | 5/2002 | Mazor et al. |
| 6,453,006 | B1 | 9/2002 | Koppel et al. |
| 6,459,763 | B1 | 10/2002 | Koinuma et al. |
| 6,504,902 | B2 | 1/2003 | Iwasaki et al. |
| 6,507,634 | B1 | 1/2003 | Koppel et al. |
| 6,512,814 | B2 | 1/2003 | Yokhin et al. |
| 6,556,652 | B1 | 4/2003 | Mazor et al. |
| 6,574,305 | B2 | 6/2003 | Boer et al. |
| 6,625,250 | B2 | 9/2003 | Houge |
| 6,639,968 | B2 | 10/2003 | Yokhin et al. |
| 6,643,354 | B2 | 11/2003 | Koppel et al. |
| 6,665,372 | B2 | 12/2003 | Bahr et al. |
| 6,680,996 | B2 | 1/2004 | Yokhin et al. |
| 6,711,232 | B1 | 3/2004 | Janik |
| 6,718,008 | B1 | 4/2004 | He et al. |
| 6,744,850 | B2 | 6/2004 | Fanton et al. |
| 6,744,950 | B2 | 6/2004 | Aleksoff |
| 6,750,952 | B2 | 6/2004 | Grodnensky et al. |
| 6,754,304 | B1 | 6/2004 | Kumakhov |
| 6,754,305 | B1 | 6/2004 | Rosencwaig et al. |
| 6,768,785 | B2 | 7/2004 | Koppel et al. |
| 6,771,735 | B2 | 8/2004 | Janik et al. |
| 6,807,251 | B2 | 10/2004 | Okanda et al. |
| 6,810,105 | B2 | 10/2004 | Nasser-Ghodsi et al. |
| 6,813,338 | B2 | 11/2004 | Harada et al. |
| 6,879,051 | B1 | 4/2005 | Singh et al. |
| 6,895,075 | B2 | 5/2005 | Yokhin et al. |
| 6,898,270 | B2 | 5/2005 | Lange et al. |
| 6,937,694 | B2 | 8/2005 | Yokoyama et al. |
| 6,947,520 | B2 | 9/2005 | Yokhin et al. |
| 6,963,630 | B2 | 11/2005 | Umezawa et al. |
| 6,970,532 | B2 | 11/2005 | Hayashi et al. |
| 6,987,832 | B2 | 1/2006 | Koppel et al. |
| 6,996,208 | B2 | 2/2006 | Helming et al. |
| 6,999,557 | B2 | 2/2006 | Yamaguchi et al. |
| 7,003,075 | B2 | 2/2006 | Miyake et al. |
| 7,035,373 | B2 | 4/2006 | Omote |
| 7,062,013 | B2 | 6/2006 | Berman et al. |
| 7,068,753 | B2 | 6/2006 | Berman et al. |
| 7,076,024 | B2 | 7/2006 | Yokhin |
| 7,110,491 | B2 | 9/2006 | Mazor et al. |
| 7,113,566 | B1 | 9/2006 | Peled et al. |
| 7,116,754 | B2 | 10/2006 | Lischka et al. |
| 7,120,227 | B2 | 10/2006 | Ozawa et al. |
| 7,120,228 | B2 | 10/2006 | Yokhin et al. |
| 7,158,608 | B2 | 1/2007 | Kucharczyk |
| 7,213,686 | B2 | 5/2007 | Kaufman |
| 7,231,016 | B2 | 6/2007 | Berman et al. |
| 7,242,743 | B2 | 7/2007 | Fewster |
| 7,242,745 | B2 | 7/2007 | He et al. |
| 7,258,485 | B2 | 8/2007 | Nakano et al. |
| 7,406,153 | B2 | 7/2008 | Berman |
| 7,474,732 | B2 | 1/2009 | Berman et al. |
| 7,483,513 | B2 | 1/2009 | Mazor et al. |
| 7,551,719 | B2 | 6/2009 | Yokhin et al. |
| 7,742,564 | B2 | 6/2010 | Parham et al. |
| 2003/0123610 | A1 | 7/2003 | Okanda et al. |
| 2003/0128809 | A1* | 7/2003 | Umezawa et al. ............ 378/70 |
| 2003/0157559 | A1 | 8/2003 | Omote et al. |
| 2006/0062351 | A1* | 3/2006 | Yokhin et al. ................ 378/86 |

FOREIGN PATENT DOCUMENTS

| | | |
|---|---|---|
| JP | 666741 A | 3/1994 |
| JP | 6258260 A | 9/1994 |
| JP | 6273357 A | 9/1994 |
| JP | 7311163 A | 11/1995 |
| JP | 8-313458 A | 11/1996 |
| JP | 9-229879 A | 9/1997 |
| JP | 10048398 A | 2/1998 |
| JP | 10160688 A | 6/1998 |
| JP | 10206354 A | 8/1998 |
| JP | 10318949 A | 12/1998 |
| JP | 1114562 A | 1/1999 |
| JP | 11014561 A | 1/1999 |
| JP | 11304728 A | 11/1999 |
| JP | 200088776 A | 3/2000 |
| JP | 2000266698 A | 9/2000 |
| JP | 2000292379 A | 10/2000 |
| JP | 2000314708 A | 11/2000 |
| JP | 200166398 A | 3/2001 |
| JP | 2001153822 A | 6/2001 |
| JP | 2003194741 A | 7/2003 |
| JP | 2003329619 A | 11/2003 |
| JP | 2004257914 A | 9/2004 |
| JP | 2005326261 A | 11/2005 |
| JP | 2006317249 A | 11/2006 |
| WO | 2004013867 A2 | 2/2004 |

OTHER PUBLICATIONS

Japanese Patent Application # 2006194756 Official Action dated Jul. 26, 2011.

U.S. Appl. No. 13/180,568, filed Jul. 12, 2011.

He, B., "Two-dimensional X-ray Diffraction", pp. 356-359, Published by John Wiley & Sons, Inc, USA, 2009.

Bowen et al., "X-Ray metrology by Diffraction and Reflectivity," CP550, Characterization and Metrology for ULSI Technology: 2000 International Conference, pp. 570-579, American Institute of Physics, 2001.

Cohen et al., "Characterization of the silicon on insulator film in bonded wafers by high resolution x-ray diffraction", Applied Physics Letters, vol. 75, No. 6, pp. 787-789, Aug. 9, 1999.

Cohen et al., "High-Resolution X-Ray Diffraction for Characterization and Monitoring of Silicon-on-Insulator Fabrication Processes," Journal of Applied Physics, vol. 93, No. 1, pp. 245-250, Jan. 1, 2003.

Goorsky et al., "Grazing Incidence In-plane Diffraction Measurement of In-plane Mosaic with Microfocus X-ray Tubes", Crystal Research and Technology, vol. 37, No. 7, pp. 645-653, year 2002.

Hayashi et al., "Refracted X-Rays Propagating Near the Surface under Grazing Incidence Condition," Spectrochimica Acta, Part B 54, pp. 227-230, year 1999.

Hu et al., "Small angle x-ray scattering metrology for sidewall angle and cross section of nanometer scale line gratings," Journal of Applied Physics, vol. 96, No. 4, pp. 1983-1987, Aug. 15, 2004.

Guerault, H., "Specular reflectivity and off-specular scattering: Tools for roughness investigation", Instituut voor Kern—en Stralingsfysica, Dec. 15, 2000.

Jones et al., "3-Dimensional Lineshape Metrology Using Small Angle X-ray Scattering", AIP Conference Proceedings, vol. 683, pp. 434-438, Sep. 30, 2003.

Jones et al., "Sub-Nanometer Wavelength Metrology of Lithographically Prepared Structures: A Comparison of Neutron and X-Ray Scattering", Proceedings of SPIE—the International Society for Optical Engineering, Jun. 1, 2003.

Jones et al., "Small Angle X-ray Scattering for Ssub-100 nm Pattern Characterization," Applied Physics Letters, vol. 83, No. 19, pp. 4059-4061, Nov. 10, 2003.

Jordan Valley, "How to Measure SiGe on SOI on BedeMetrixTM Tools", Electronic Materials Conference 2008, USA, Jul. 21, 2008.

Kojima et al., "Structural Characterization of Thin Films by X-ray Reflectivity," Rigaku Journal, vol. 16, No. 2, pp. 31-41, year 1999.

Kozaczek et al., "X-ray Diffraction Metrology for 200mm Process Qualification and Stability Assessment," Advanced Metallization Conference, Canada, Oct. 8-11, 2001.

X-Ray Optical Systems, Inc., "Monolithic Polycapillary Lens Information", Albany, USA, Dec. 29, 1998.

Wu et al., "Substepping and its Application to HST Imaging", Astronomical Data Analysis Software and Systems VII ASP Conference Series, vol. 145, pp. 82-85, year 1998.

Naudon et al., "New Apparatus for Grazing X-ray Reflectometry in the Angle-Resolved Dispersive Mode," Journal of Applied Crystallography, vol. 22, pp. 460-464, year 1989.

Neissendorfer et al., "The Energy-Dispersive Reflectometer/Diffractometer at BESSY-I", Measurement Science Technology, vol. 10, pp. 354-361, IOP Publishing Ltd., year 1999.

Parrill et al., "GISAXS—Glancing Incidence Small Angle X-ray Scattering," Journal de Physique IV, vol. 3, pp. 411-417, Dec. 1993.

Powell et al., "X-ray Diffraction and Reflectivity Characterization of SiGe Superlattice", Semiconductor Science Technology Journal, vol. 7, pp. 627-631, year 1992.

Di Fonzo et al., "Non-Destructive Determination of Local Strain with 100-Nanometre Spatial Resolution," Nature, vol. 403, pp. 638-640, Feb. 10, 2000.

Ulyanenkov, A., "Introduction to High Resolution X-Ray Diffraction," Workshop on X-ray characterization of thin layers, Uckley, May 21-23, 2003.

Authier, A., "Dynamical Theory of X-Ray Diffraction", International Union of Crystallography, Monographs on Crystallography 11, revised edition, Oxford University Press 2005.

Wiener et al., "Characterization of Titanium Nitride Layers by Grazing- Emission X-Ray Fluorescence Spectrometry", Applied Surface Science, vol. 125, pp. 129-136, Elsevier Science BV 1998.

Woitok et al., "Towards Fast Reciprocal Space Mapping," JCPDS—International Centre for Diffraction Data, Advances in X-ray Analysis, vol. 48, pp. 165-169, year 2005.

Oxford Instruments Inc., Series 5000 Model XTF5011 X-Ray Tube Datasheet, Scotts Valley, USA, Jun. 28, 2000.

Japanese Patent Application # 2003549898 Official Action dated Jun. 7, 2010.

U.S. Appl. No. 09/941,723 Official Action dated Apr. 4, 2005.
U.S. Appl. No. 10/946,426 Official Action dated Feb. 6, 2006.
U.S. Appl. No. 11/018,352 Official Action dated Feb. 8, 2006.
U.S. Appl. No. 11/018,352 Official Action dated Oct. 24, 2005.
U.S. Appl. No. 11/200,857 Official Action dated Aug. 11, 2008.
U.S. Appl. No. 11/200,857 Official Action dated Aug. 27, 2007.
U.S. Appl. No. 11/200,857 Official Action dated Mar. 11, 2008.
U.S. Appl. No. 11/389,490 Official Action dated May 1, 2008.
U.S. Appl. No. 11/487,433 Official Action dated May 29, 2008.

Ryan et al., U.S. Appl. No. 61/328,645 "High-Resolution X-Ray Diffractometer" filed Apr. 28, 2010.

Japanese Patent Application # 2005274293 Official Action dated Dec. 21, 2010.

Japanese Patent Application # 2005273641 Official Action dated Oct. 28, 2010.

U.S. Appl. No. 12/683,436 "HRXRD measurement with enhanced sensitivity" filed Jan. 7, 2011.

Pesek et al., "Lattice Misfit and Relative Tilt of Lattice Planes in Semiconductor Heterostructures", Semiconductor Science and Technology Journal, vol. 6, pp. 705-708, IOP Publishing Ltd 1991.

Korean Patent Application # 10-2005-0083542 Office Action dated Feb. 15, 2012.

U.S. Appl. No. 12/683,436 Office Action dated Jan. 23, 2012.

* cited by examiner

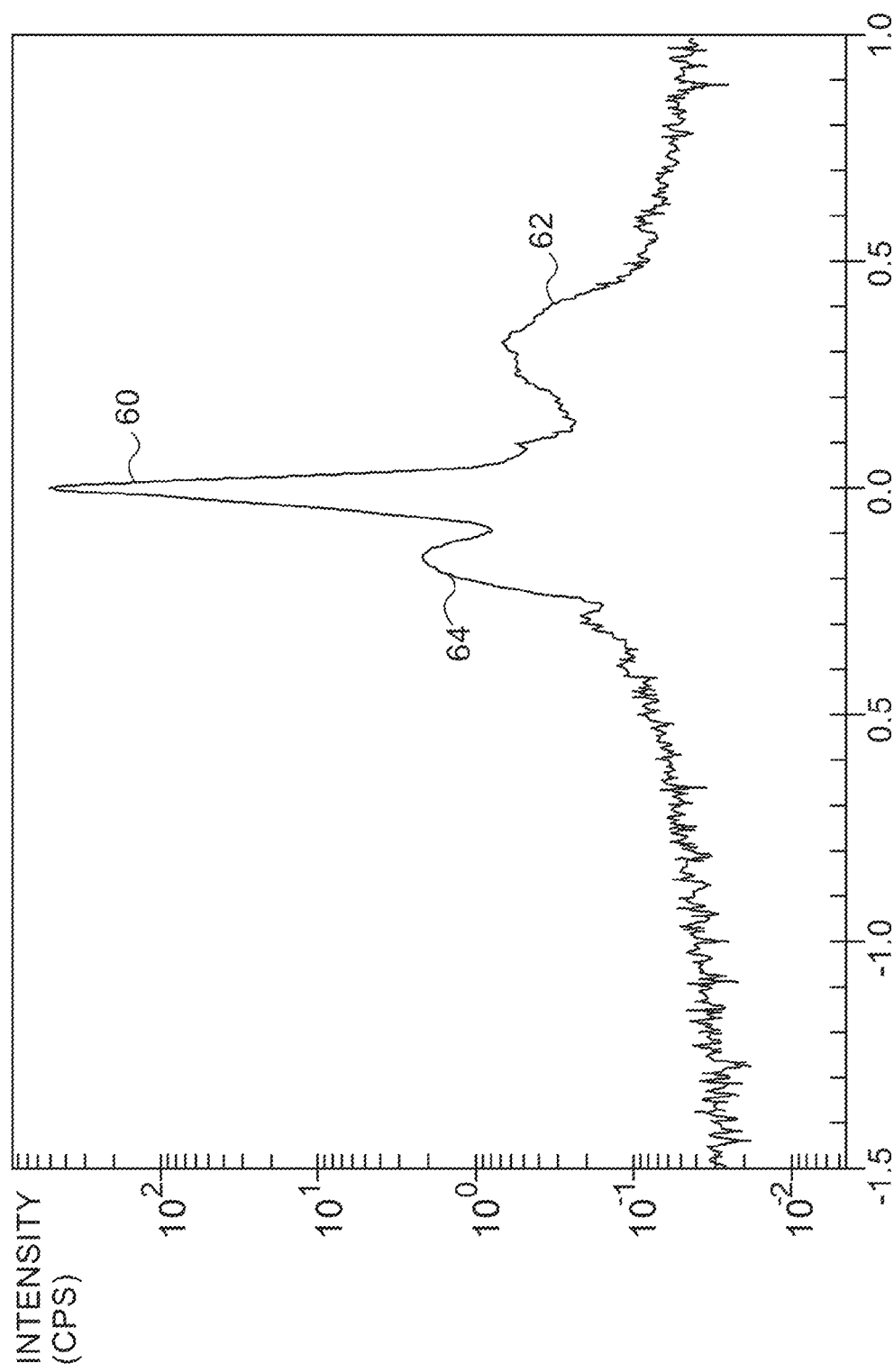

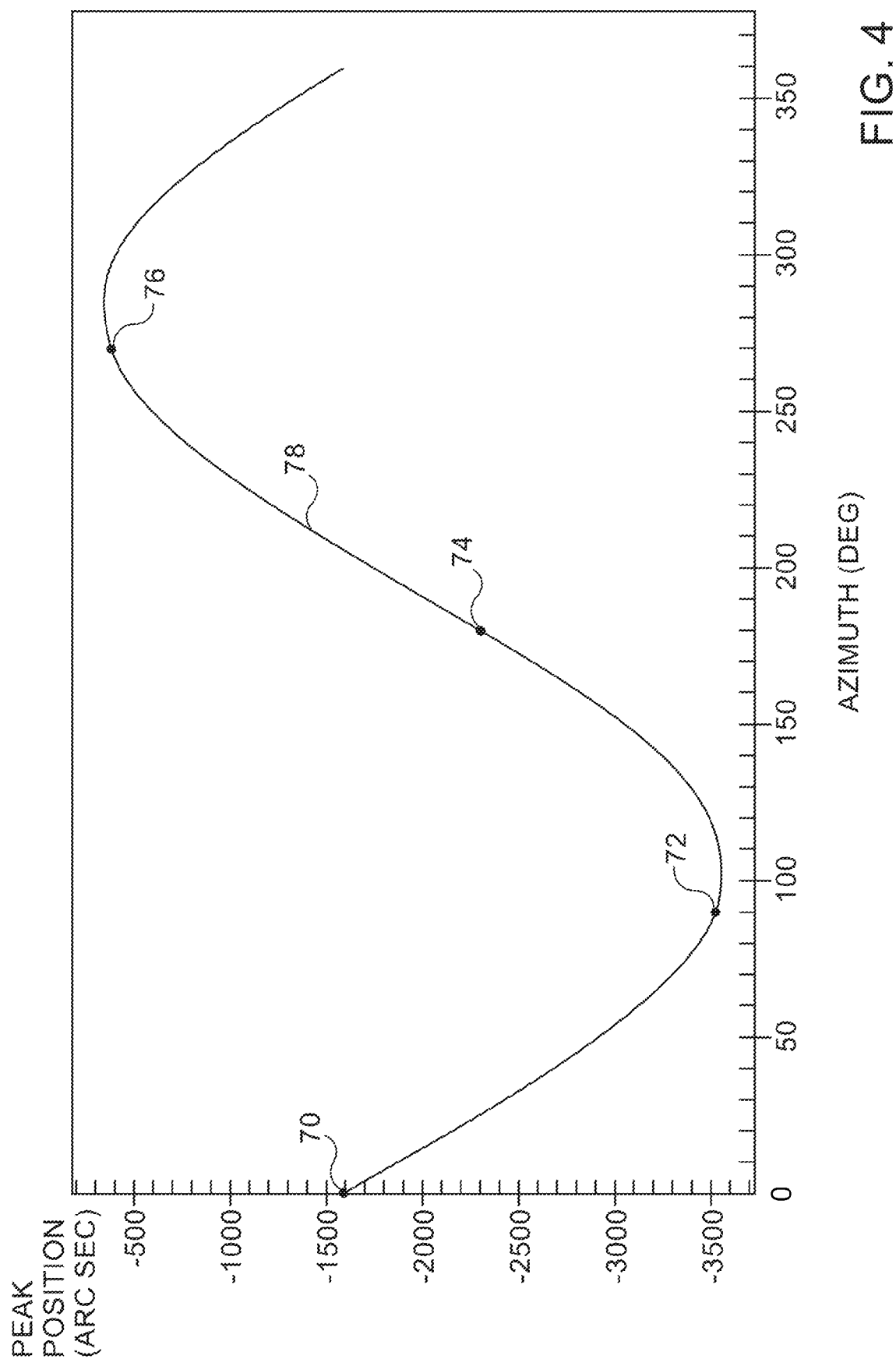

FAST MEASUREMENT OF X-RAY DIFFRACTION FROM TILTED LAYERS

FIELD OF THE INVENTION

The present invention relates generally to X-ray analysis, and specifically to X-ray measurement of thin film properties.

BACKGROUND OF THE INVENTION

X-ray diffractometry (XRD) is a well-known technique for studying the crystalline structure of matter. In XRD, a sample is irradiated by a monochromatic X-ray beam, and the locations and intensities of the diffraction peaks are measured. The characteristic diffraction angles and the intensity of the diffracted radiation depend on the lattice planes of the sample under study and the atoms that make up the crystalline material. For a given wavelength $\lambda$ and lattice plane spacing d, diffraction peaks will be observed when the X-ray beam is incident on a lattice plane at angles $\theta$ that satisfy the Bragg condition: $n\lambda = 2d \sin \theta_B$, wherein n is the scattering order. The angle $\theta_B$, that satisfies the Bragg condition is known as the Bragg angle. Distortions in the lattice planes due to stress, solid solution, or other effects lead to observable changes in the XRD spectrum.

XRD has been used, inter alia, for measuring characteristics of single-crystal layers produced on semiconductor wafers. In some of these measurements, relative angular tilt between the layers is taken into account. For example, Pesek et al. describe XRD techniques of this sort in "Lattice Misfit and Relative Tilt of Lattice Planes in Semiconductor Heterostructures," *Semiconductor Science and Technology* 6 (1991), pages 705-708, which is incorporated here by reference. The authors used XRD to investigate the tilt in various compound semiconductor layers grown on miscut GaAs substrates.

Cohen et al. describe similar techniques in "High-Resolution X-Ray Diffraction for Characterization and Monitoring of Silicon-on-Insulator Fabrication Processes," *Journal of Applied Physics* 93 (2003), pages 245-250, which is also incorporated herein by reference. The authors found XRD to be applicable to multilayered silicon-on-insulator (SOI) structures fabricated by wafer bonding. The tilt and rotation of each crystalline layer with respect to the substrate allowed them to obtain independent measurements of each SOI film.

SUMMARY

Embodiments of the present invention that are described hereinbelow provide improved methods and devices for fast, high-resolution XRD (HRXRD).

There is therefore provided, in accordance with an embodiment of the present invention, a method for analysis, that includes directing a converging beam of X-rays toward a surface of a sample having multiple single-crystal layers, including at least a first layer and a second layer that is formed over and tilted relative to the first layer. The X-rays that are diffracted from each of the first and second layers are sensed simultaneously, while resolving the sensed X-rays as a function of angle so as to generate a diffraction spectrum including at least a first diffraction peak due to the first layer and a second diffraction peak due to the second layer. The diffraction spectrum is analyzed so as to identify a characteristic of at least the second layer.

Typically, sensing the X-rays includes deploying a detector array having elements configured to capture and resolve the X-rays over a range of elevation angles simultaneously, wherein the range is at least 2 degrees.

In some embodiments, sensing the X-rays includes detecting the X-rays over a range of elevation angles at two or more different azimuthal angles so as to generate at least first and second diffraction spectra at first and second azimuthal angles, respectively. Analyzing the diffraction spectrum may then include comparing the first and second diffraction spectra so as to quantify a tilt of the second layer relative to the first layer. In one embodiment, comparing the diffraction spectra includes finding angular locations of the diffraction peaks as a function of the azimuthal angles, and fitting the angular locations to a parametric formula in order to find at least one of a magnitude and a direction of the tilt. Alternatively or additionally, directing the converging beam includes adjusting an azimuthal orientation between the sample and the beam so as to nullify an effect of the tilt on the diffraction spectrum. Typically, the tilt causes a separation between angular locations of the first and second diffraction peaks to vary as a function of the azimuthal angles, and comparing the diffraction spectra may further alternatively or additionally include correcting a measured value of the separation responsively to the quantified tilt.

In a disclosed embodiment, analyzing the diffraction spectrum includes identifying a strain in the second layer.

In one embodiment, a third layer is formed over the second layer, so that the diffraction spectrum includes a third diffraction peak due to the third layer, and analyzing the diffraction spectrum includes finding a property of the third layer responsively to a displacement between the second and third diffraction peaks.

There is also provided, in accordance with an embodiment of the present invention, apparatus for analysis, including an X-ray source, which is configured to direct a converging beam of X-rays toward a surface of a sample having multiple single-crystal layers, including at least a first layer and a second layer that is formed over and tilted relative to the first layer. A detector assembly is configured to simultaneously sense the X-rays that are diffracted from each of the first and second layers while resolving the sensed X-rays as a function of angle so as to generate a diffraction spectrum including at least a first diffraction peak due to the first layer and a second diffraction peak due to the second layer. A processor is coupled to analyze the diffraction spectrum so as to identify a characteristic of at least the second layer.

The present invention will be more fully understood from the following detailed description of the embodiments thereof, taken together with the drawings in which:

BRIEF DESCRIPTION OF THE DRAWINGS

FIGS. 3A and 3B are schematic representations of HRXRD spectra obtained at different azimuthal angles from a sample having tilted layers, in accordance with an embodiment of the present invention; and FIG. 4 is a plot that schematically shows a variation in peak position as a function of azimuthal angle in HRXRD spectra obtained from a sample having tilted layers, in accordance with an embodiment of the present invention.

DETAILED DESCRIPTION OF EMBODIMENTS

When XRD measurements are to be made on tilted layers using conventional methods of detection, painstaking adjustment and scanning of the X-ray sample and detection angles are generally required. The diffraction spectrum must typically be measured first at one rocking angle to find the substrate spectrum and, for highly tilted layers, at another, different angle to find the spectrum of the tilted layer. Finding the correct angles often entails a lengthy process of trial and error, and it is possible that spectral components due to tilted layers may be missed entirely.

Embodiments of the present invention that are described hereinbelow provide improved methods and systems for use in fast HDXRD measurement and analysis of tilted epitaxial films on a sample. "Tilt" in this context refers to non-parallel orientation of the crystal planes of the film relative to the planes of an underlying layer. In one embodiment, for example, the sample is a silicon wafer in which the silicon substrate constitutes a first layer, and a second layer comprising an epitaxial film is formed over the substrate. Thus, references to a "layer" in the description and claims that follow should be understood, where appropriate, to refer to the substrate, as well. The second layer may be tilted relative to the first layer either by design, or due to imperfections in the fabrication process. Alternatively, the methods and systems described herein may be applied to samples and crystalline layers (including, but not limited to, epitaxial films) of other types.

An X-ray source directs a converging beam of X-rays toward the surface of the sample. A detector assembly senses the X-rays that are diffracted from each of the first and second layers (including the substrate "layer," as noted above), while resolving the sensed X-rays as a function of angle. For this purpose, the detector assembly typically comprises an array of detector elements, which detect the diffracted X-rays at different, respective elevation angles. The detector assembly thus generates a diffraction spectrum, which includes respective diffraction peaks due to at least the first and second layers. Because the system both irradiates and detects the scattered X-rays over a range of angles simultaneously, the entire spectrum, including the Bragg diffraction peaks due to two (or more) different layers, can be captured rapidly in a single position of the source and detector assemblies, without the need for mechanical scanning. A processor analyzes the diffraction spectrum in order to identify characteristics of the tilted layer or layers.

Figure 1:
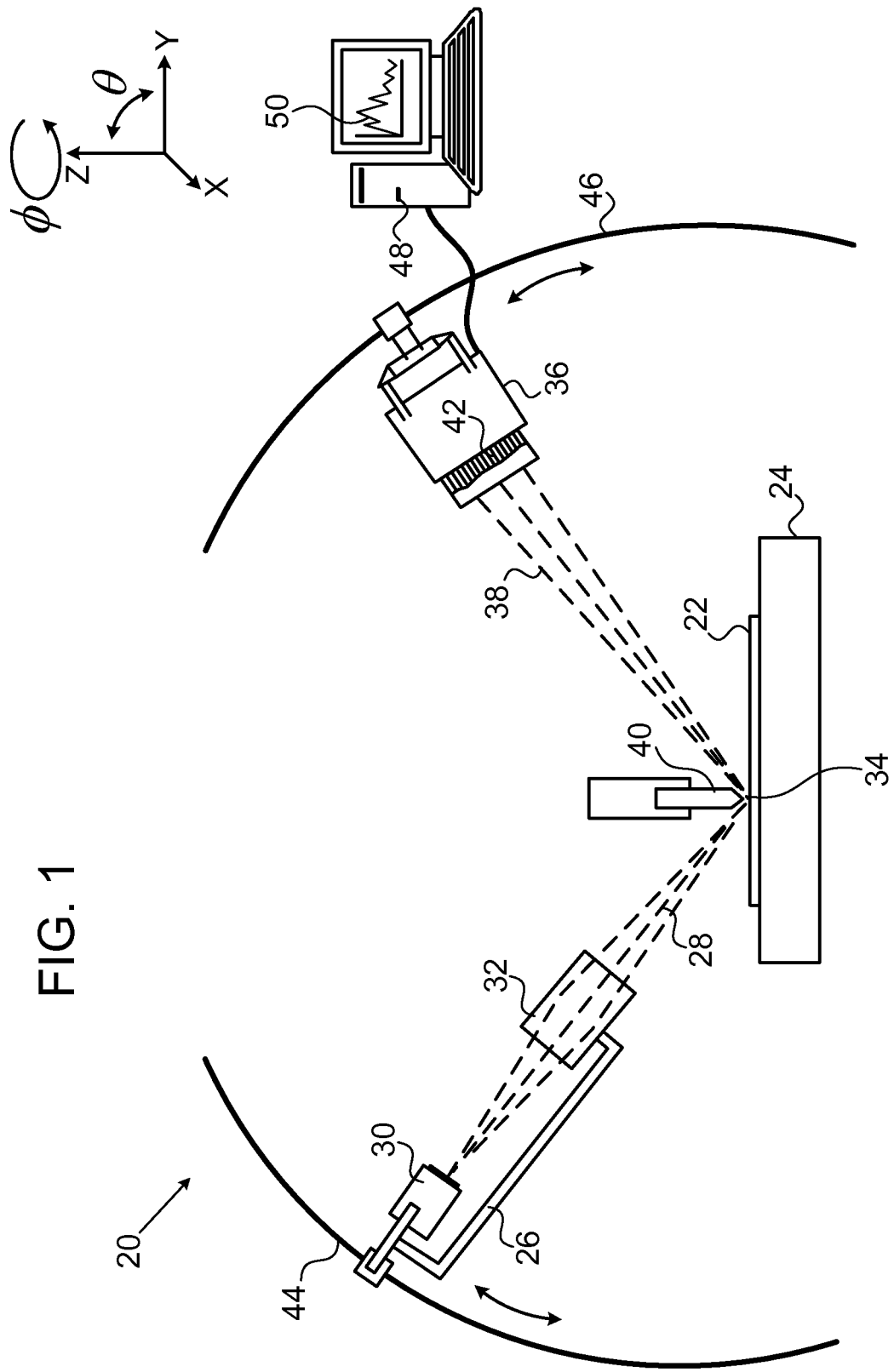
FIG. 1 is a schematic side view of an X-ray metrology system, in accordance with an embodiment of the present invention.

FIG. 1 is a schematic side view of a system 20 for HDXRD of a sample 22, in accordance with an embodiment of the present invention. Sample 22 is mounted on a motion stage 24, allowing accurate adjustment of the position and orientation of the sample. An X-ray source 26 directs a converging X-ray beam 28 toward a small area 34 on sample 22. Typically, source 26 comprises an X-ray tube 30 with suitable optics 32 to focus and monochromatize beam 28. Beam 28 typically subtends at least 2°, and may subtend as much as 4° or even more, depending on optics 32, in order to irradiate sample 22 over a large range of angles simultaneously.

X-rays are diffracted from sample 22 in a generally diverging beam 38, which is received by a detector assembly 36. The detector assembly typically comprises a detector array 42, such as a CCD array, comprising multiple detector elements, configured so as to resolve beam 38 as a function of elevation angle θ. Typically, the angular span of array 42 is comparable to that of beam 28, i.e., at least 2°, and possibly 4° or greater. A knife edge 40 and/or other optical elements may be used to limit beam 28 and/or beam 38 and block undesired scattered radiation that might otherwise strike array 42 and interfere with the diffraction measurement.

Various types of X-ray sources and detector assemblies may be used in system 20. Details of such components are described, for example, in U.S. Pat. Nos. 7,076,024, 7,120, 228 and 7,551,719, whose disclosures are incorporated herein by reference.

The positions of source 26 and detector assembly 36 are controlled by motion assemblies 44 and 46, respectively. In the simplified view shown in FIG. 1, the motion assemblies comprise curved tracks, which permit the source and detector assembly to be positioned at the appropriate elevations, typically in the vicinity of the Bragg angles of the layers that are to be analyzed. Other suitable motion assemblies will be apparent to those skilled in the art. For the sake of this example, it is assumed that the lattice planes creating the diffraction pattern are approximately parallel to the surface of sample 22, so that the incidence and takeoff angles defined by beams 28 and 38 relative to the surface are both equal to the Bragg angle. Alternatively, source 26 and detector assembly 38 may be positioned at different incidence and takeoff angles in order to measure diffraction from lattice planes that are not parallel to the surface of sample 22.

In addition, as noted above, stage 24 may be configured to translate the X-Y location on the sample that falls within area 34, as well as to rotate the azimuthal angle φ of the sample relative to beam 28. (As shown in FIG. 1, the X-Y plane is taken to be the sample surface, with the Z-axis perpendicular to the surface; θ is the elevation angle relative to the Z-axis; and φ is the azimuthal angle of rotation about the Z-axis.)

A signal processor 48 receives and analyzes the output of assembly 36, so as to measure a spectrum 50 of the flux of X-ray photons diffracted from sample 22 as a function of angle at a given energy or over a range of energies. Typically, sample 22 has one or more thin surface layers, such as thin films, at area 34, so that distribution 50 as a function of elevation angle exhibits a structure that is characteristic of diffraction effects due to the surface layer and underlying layers. Processor 48 analyzes the angular spectrum in order to determine characteristics of one or more of the layers of the sample, such as the composition, thickness, lattice strain and/or tilt angle of the layer, using methods of analysis described hereinbelow.

The components of system 20 and the techniques described herein may be integrated into systems that provide other types of measurement functionality, such as X-ray reflectometry and scattering measurements. Additionally or alternatively, these components and techniques may be integrated as process monitoring tools in manufacturing systems, such as systems for semiconductor wafer fabrication. Integrated systems of these types are described in greater detail in the above-mentioned patents.

Figure 2A:
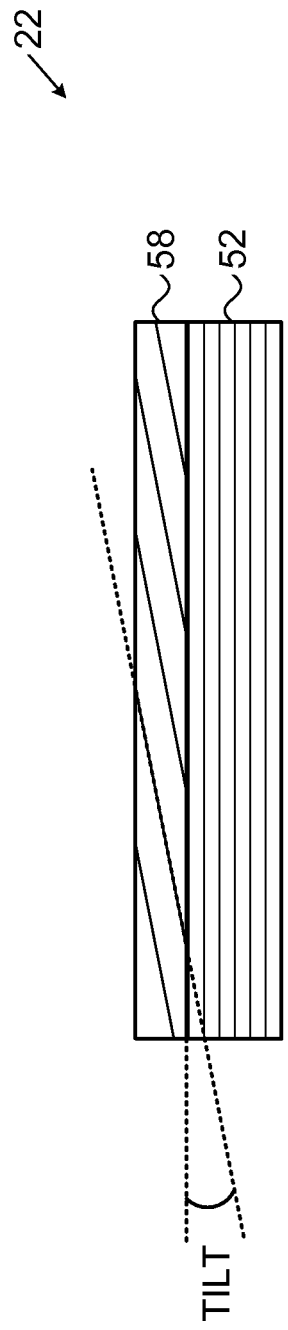
FIGS. 2A and 2B are schematic sectional views of semiconductor wafers showing details of layers formed thereon, whose properties are analyzed in accordance with an embodiment of the present invention.
Figure 2B:
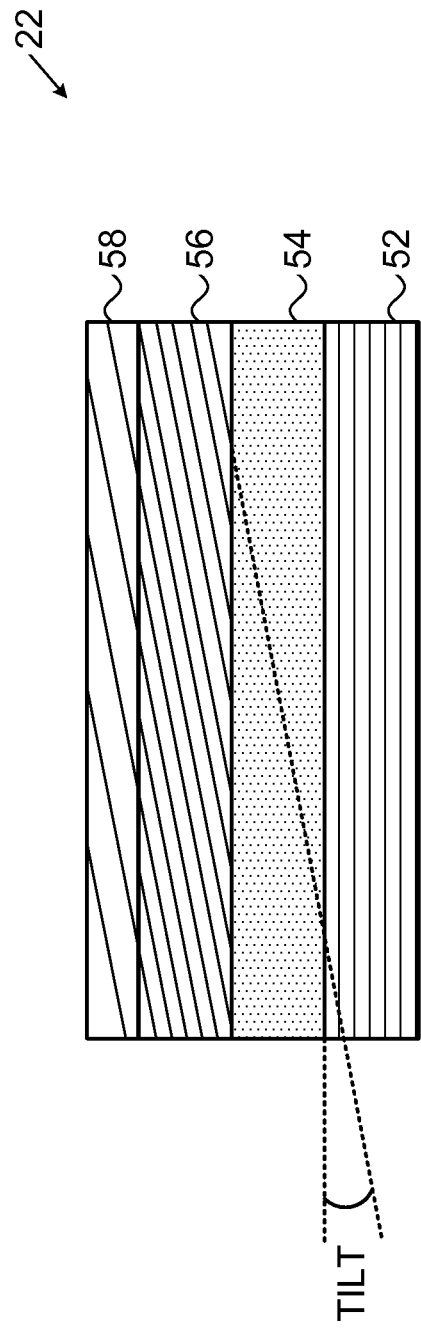

FIGS. 2A and 2B are schematic sectional views of sample 22, showing two examples of layers formed on the sample. The properties of these layers are analyzed in accordance with embodiments of the present invention that are described below. In these embodiments, the sample is a silicon wafer (which is referred to as a substrate 52, or alternatively as a carrier layer, as explained above). In FIG. 2A, a SiGe layer 58 is formed on substrate 52. In FIG. 2B, a buried oxide (BOX) insulating layer 54 is formed over substrate 52, and a silicon-on-insulator (SOI) layer 56 is deposited on the BOX layer. SiGe layer 58 is then formed on the SOI layer.

Sample 22 is analyzed in system 20 in order to find the diffraction angle of SiGe layer 58, which varies as a function of the layer composition and thus gives an indication of the germanium concentration. The diffraction angle will, however, be offset from the Bragg angle if the lattice planes in layer 58 are rotated (tilted) with respect to the corresponding planes in the underlying substrate 52. In the case of bulk substrates, tilt in layer 58 may arise when it is grown on a substrate whose surface is inclined relative to a major crystallographic plane, i.e., a miscut substrate. The Bragg angle may also be affected by strain in SOI layer 56, resulting in changes in the lattice spacing in both layer 56 and layer 58. These offsets are overcome by the ability of system 20 to capture high-resolution XRD spectra over a range of elevation angles, as illustrated in the figures that follow.

Figure 3B:
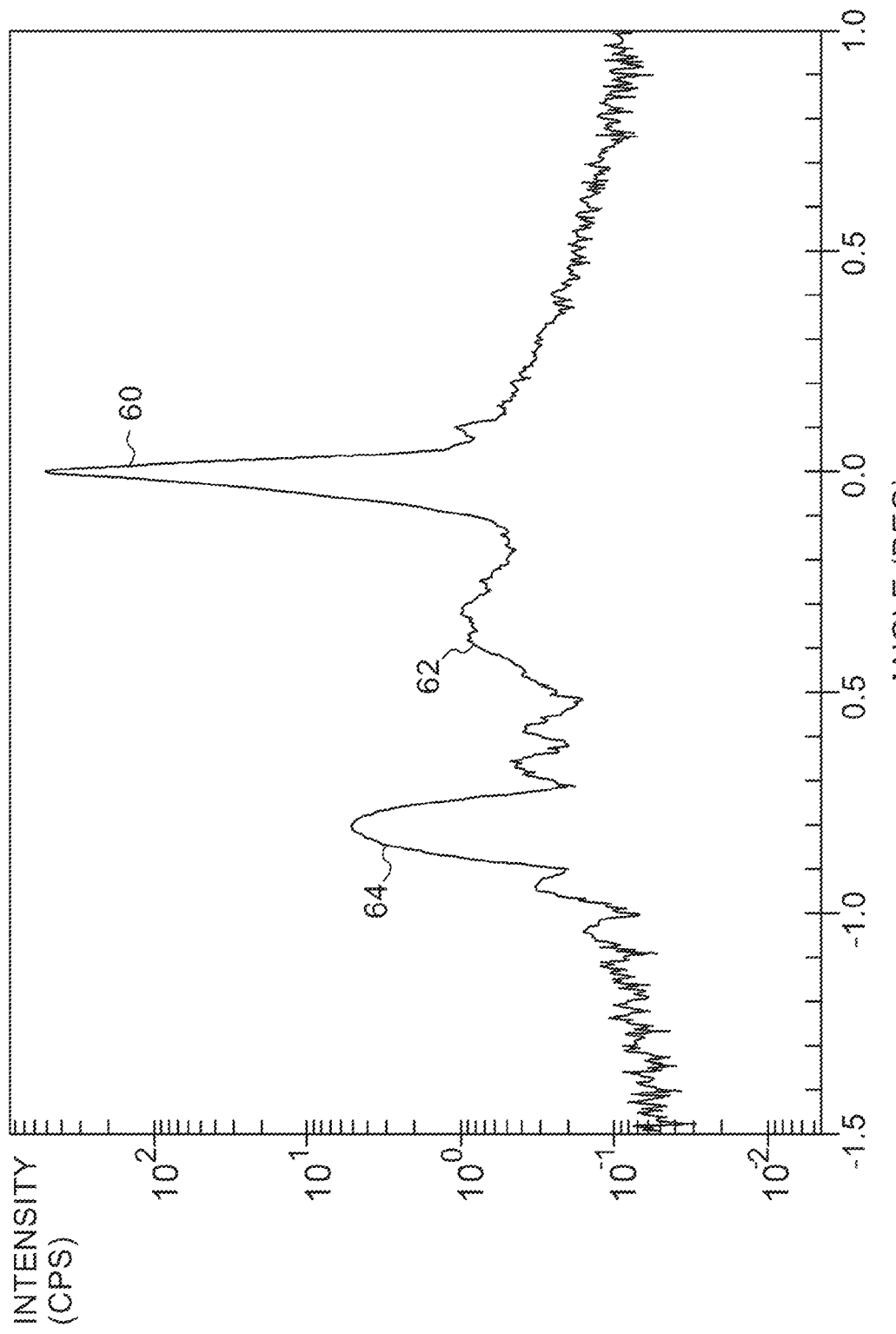

FIGS. 3A and 3B are schematic representations of HRXRD spectra obtained at different azimuthal angles from sample 22, having tilted layers as shown in FIG. 2B, in accordance with an embodiment of the present invention. The spectra are shown on a logarithmic scale in counts per second (CPS) captured by the elements of array 42, as a function of the respective elevation angles of the elements. The angular scale is adjusted, for the sake of convenience, so that a peak 60 due to diffraction from substrate layer 52 is taken as the origin ($\theta=0$).

A second peak 62 due to SOI layer 56 is offset relative to peak 60 as the result of the tilt in layer 54 and possibly lattice strain in layer 56. This offset varies with azimuthal angle, as shown by the difference in peak positions between FIGS. 3A and 3B. There is little or no tilt (less than 1 arc minute), however, between layers 56 and 58. Therefore, the offset between peak 62 and a peak 64 due to SiGe layer 58 (which is about 0.5°) remains constant and indicates accurately the concentration of germanium in the layer. Thus, because layer 56 is available to serve as a reference, there is no need in this example to actually measure the tilt in order to extract the desired diffraction data with respect to layer 58.

Alternatively, the difference in peak positions in spectra taken at different azimuthal angles can be used to measure the layer tilt explicitly. Because of the change of the azimuth between FIGS. 3A and 3B, peaks 62 and 64 in the two spectra, due to SOI layer 56 and SiGe layer 58, are shifted with respect to substrate peak 60. This varying angular shift of the layer peak positions relative to that of the underlying substrate is expected, since the inclination angles of layers 56 and 58 are reversed with respect to the substrate layer 52 when the sample is rotated 180° in $\phi$ (about an axis normal to the surface of the substrate 52, corresponding to right/left reversal in FIG. 2B).

Measurements of the dependence of peak offset on the azimuth can be applied to calculate the relative tilt between the layers. The offset of either peak 62 or 64 can be used for this purpose, depending on the detailed structure of sample 22. In the present example peak 64, due to SiGe layer 58, would probably be chosen for tilt measurement, since this layer is thicker, and the peak is sharper and more intense; hence its position can be determined more precisely.

FIG. 4 is a plot that schematically shows a variation in relative peak positions as a function of azimuthal angle in HRXRD spectra obtained from the tilted layers of sample 22, in accordance with an embodiment of the present invention. Data points 70, 72, 74 and 76 indicate the position of peak 64, due to SiGe layer 58, relative to substrate peak 60, measured at four different azimuths. A curve 78 is fitted to the data points in accordance with a parametric model, which is described below. This fit gives a tilt angle of 1608 arcsec.

The relative tilt between the planes in layer 58 and corresponding planes in substrate 52 is obtained by the following relationship:

$$\text{Tilt}=[\Delta\theta(\phi)+\Delta\theta(\phi+180)]/2 \quad (1)$$

wherein $\Delta\theta(\phi)$ is the angular separation between layer peak 64 (or 62) and substrate peak 60 measured at azimuth $\phi$.

Additional measurements at other azimuthal angles can be used to further improve the estimation of the tilt and also to determine its direction with respect to a reference point, such as an orientation notch on sample 22. In this case, the measured angular separations $\Delta\theta(\phi)$ between the peaks as a function of azimuth $\phi$ are fitted to the following parametric formula:

$$\Delta\theta(\phi)=\Delta\theta_0+\text{TiltMagnitude}\times\cos(\phi+\text{TiltDirection}) \quad (2)$$

The constant ($\Delta\theta_0$), TiltMagnitude and TiltDirection parameters can be fitted, using a non-linear regression algorithm, to three or more measurements of the layer-to-substrate peak separations. A fit of this sort is illustrated in FIG. 4.

The tilt that is measured in this manner can be used in finding the peak separation with improved accuracy, which in turn gives a more accurate value of the strain and/or composition of layer 58. There are a number of ways in which tilt and peak separation can be measured and used, depending, inter alia, on the capabilities of the HDXRD measurement system.

Assuming, for example, that stage 24 is capable of moving sample 22 so that beam 28 can access all sites (x,y) on the sample at all azimuths $\phi$, then the method described above can be used to measure the tilt at each and every site on the wafer. The measured peak separation $\Delta\theta(\phi)$ is adjusted accordingly to give the corrected separation:

$$\Delta\theta'(\phi)=\Delta\theta(\phi)-\text{Tilt}$$

Here Tilt is determined for the specific azimuth $\phi$. This approach may be useful if the magnitude of the tilt varies significantly across the surface of sample 22, but it reduces the throughput of system 20 since at least two measurements are required at all sites.

An alternative method is to find the tilt properties at a single site and then apply this tilt to all subsequent measurement points. This approach can be employed if the capabilities of stage 24 are limited or in order to improve throughput. This method is useful, for example, if stage 24 does not allow all azimuth values $\phi$ to be accessed at all sites (x,y) on the wafer. In this case it is assumed that the tilt does not vary significantly across the surface of the sample and may be regarded as a constant value for a specific azimuth.

As a further alternative, the tilt magnitude and direction may be determined using three or more measurements at a single site on the wafer. This information is then applied in driving stage 24 to set the azimuthal orientation of sample 22 such that the effect of the tilt, as described in equation (2), is nullified. This condition is satisfied when the sample azimuth is oriented at a right angle ($\pm 90°$) with respect to the fitted TiltDirection. This approach can be used in measuring symmetrical reflections when the diffraction planes are almost parallel to the sample surface, as long as the TiltDirection is constant across the wafer. Thus, in this case, the effects of tilt at all measured sites are eliminated by determining the tilt properties at a single site. When the sample azimuth is oriented in this way, it does not matter if the TiltMagnitude varies across the wafer, because the effective tilt at the proper azimuth will remain equal to zero.

Although the embodiments shown in the figures above relate to specific types of layer structures on a silicon wafer, the principles of the present invention are similarly applicable in making rapid XRD measurements on crystalline samples of other types in which the lattice angles may not be well controlled or precisely known in advance. It will therefore be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for analysis, comprising:
   directing a converging beam of X-rays toward a surface of a sample having multiple single-crystal layers, including at least a first layer and a second layer that is formed over and tilted relative to the first layer;
   simultaneously sensing the X-rays that are diffracted from each of the first and second layers while resolving the sensed X-rays as a function of angle so as to generate a diffraction spectrum comprising at least a first diffraction peak due to the first layer and a second diffraction peak due to the second layer,
   wherein sensing the X-rays comprises detecting the X-rays over a range of elevation angles at two or more different azimuthal angles so as to generate at least first and second diffraction spectra at first and second azimuthal angles, respectively; and
   analyzing the diffraction spectrum so as to identify a characteristic of at least the second layer,
   wherein analyzing the diffraction spectrum comprises comparing the first and second diffraction spectra so as to quantify a tilt of the second layer relative to the first layer.

2. The method according to claim 1, wherein sensing the X-rays comprises deploying a detector array having elements configured to capture and resolve the X-rays over a range of elevation angles simultaneously.

3. The method according to claim 2, wherein the range is at least 2 degrees.

4. The method according to claim 1, wherein comparing the first and second diffraction spectra comprises finding angular locations of the first and second diffraction peaks as a function of the azimuthal angles, and fitting the angular locations to a parametric formula in order to find at least one of a magnitude and a direction of the tilt.

5. The method according to claim 1, wherein directing the converging beam comprises adjusting an azimuthal orientation between the sample and the beam so as to nullify an effect of the tilt on the diffraction spectrum.

6. The method according to claim 1, wherein the tilt causes a separation between angular locations of the first and second diffraction peaks to vary as a function of the azimuthal angles, and wherein comparing the first and second diffraction spectra comprises correcting a measured value of the separation responsively to the quantified tilt.

7. The method according to claim 1, wherein analyzing the diffraction spectrum comprises identifying a strain in the second layer.

8. The method according to claim 1, wherein a third layer is formed over the second layer, and wherein the diffraction spectrum comprises a third diffraction peak due to the third layer, and wherein analyzing the diffraction spectrum comprises finding a property of the third layer responsively to a displacement between the second and third diffraction peaks.

9. Apparatus for analysis, comprising:
   an X-ray source, which is configured to direct a converging beam of X-rays toward a surface of a sample having multiple single-crystal layers, including at least a first layer and a second layer that is formed over and tilted relative to the first layer;
   a detector assembly, which is configured to simultaneously sense the X-rays that are diffracted from each of the first and second layers while resolving the sensed X-rays as a function of angle so as to generate a diffraction spectrum comprising at least a first diffraction peak due to the first layer and a second diffraction peak due to the second layer,
   wherein the detector assembly is configured to sense the X-rays over a range of elevation angles at two or more different azimuthal angles so as to generate at least first and second diffraction spectra at first and second azimuthal angles, respectively; and
   a processor, which is coupled to analyze the diffraction spectrum so as to identify a characteristic of at least the second layer,
   wherein the processor is configured to compare the first and second diffraction spectra so as to quantify a tilt of the second layer relative to the first layer.

10. The apparatus according to claim 9, wherein the detector assembly comprises a detector array having elements configured to capture and resolve the X-rays over a range of elevation angles simultaneously.

11. The apparatus according to claim 10, wherein the range is at least 2 degrees.

12. The apparatus according to claim 9, wherein the processor is configured to find angular locations of the first and second diffraction peaks as a function of the azimuthal angles, and to fit the angular locations to a parametric formula in order to find at least one of a magnitude and a direction of the tilt.

13. The apparatus according to claim 9, and comprising a stage, which is configured to adjust an azimuthal orientation between the sample and the beam so as to nullify an effect of the tilt on the diffraction spectrum.

14. The apparatus according to claim 9, wherein the tilt causes a separation between angular locations of the first and second diffraction peaks to vary as a function of the azimuthal angles, and wherein the processor is configured to correct a measured value of the separation responsively to the quantified tilt.

15. The apparatus according to claim 9, wherein the processor is configured to identify a strain in the second layer by analyzing the diffraction spectrum.

16. The apparatus according to claim 9, wherein a third layer is formed over the second layer, and wherein the diffraction spectrum comprises a third diffraction peak due to the third layer, and wherein the processor is configured to find a property of the third layer responsively to a displacement between the second and third diffraction peaks.

* * * * *